(12) United States Patent
Kusunoki et al.

(10) Patent No.: US 10,845,352 B2
(45) Date of Patent: Nov. 24, 2020

(54) SLAG VOLUME EVALUATION METHOD FOR MOLTEN METAL SURFACE

(71) Applicant: NIPPON STEEL CORPORATION, Tokyo (JP)

(72) Inventors: Tomoyuki Kusunoki, Tokyo (JP); Takahiro Miyazaki, Tokyo (JP)

(73) Assignee: NIPPON STEEL CORPOATION, Tokyo (JP)

( * ) Notice: Subject to any disclaimer, the term of this patent is extended or adjusted under 35 U.S.C. 154(b) by 0 days.

(21) Appl. No.: 16/466,154

(22) PCT Filed: Dec. 6, 2017

(86) PCT No.: PCT/JP2017/043809
§ 371 (c)(1),
(2) Date: Jun. 3, 2019

(87) PCT Pub. No.: WO2018/105652
PCT Pub. Date: Jun. 14, 2018

(65) Prior Publication Data
US 2020/0064326 A1    Feb. 27, 2020

(30) Foreign Application Priority Data

Dec. 6, 2016   (JP) ................................. 2016-236936

(51) Int. Cl.
*G01N 33/20*   (2019.01)
*G01B 11/06*   (2006.01)
(Continued)

(52) U.S. Cl.
CPC ............. *G01N 33/20* (2013.01); *G01B 11/06* (2013.01); *G01F 17/00* (2013.01); *G06T 7/001* (2013.01)

(58) Field of Classification Search
CPC ...... G01N 33/20; G01N 33/205; G01B 11/06; G01B 11/00; G01F 17/00; G01F 22/00;
(Continued)

(56) References Cited

U.S. PATENT DOCUMENTS 3,080,755 A    3/1963  Percy
5,301,621 A *  4/1994  Vassiliou .................. F23G 5/20
                                                        110/185
(Continued)

FOREIGN PATENT DOCUMENTS

CA         2250871 A1    10/1997
CN         1215357 A      4/1999
(Continued)

OTHER PUBLICATIONS

International Search Report for PCT/JP2017/043809 dated Mar. 6, 2018.
(Continued)

*Primary Examiner* — John B Strege
(74) *Attorney, Agent, or Firm* — Birch, Stewart, Kolasch & Birch, LLP (57) ABSTRACT

A slag volume evaluation method for a molten metal surface includes calculating an approximation curve indicating a correspondence between a thickness of slag and a density parameter in advance by measuring thicknesses of a plurality of pieces of the slag which float on a surface of a molten metal in a container and differ from each other in thickness, and calculating a value of the density parameter which is correlated to a density in a pixel region corresponding to the plurality of pieces of the slag in a captured image of a molten metal surface in the container; and calculating a volume of the slag by calculating and integrating the thickness of the slag for each of pixels constituting the captured image obtained by capturing an image of the molten metal surface (Continued)

which is an evaluation target, according to a value of the density parameter of each of the pixels and the approximation curve.

2 Claims, 6 Drawing Sheets

(51) Int. Cl.
  *G01F 17/00* (2006.01)
  *G06T 7/00* (2017.01)
(58) Field of Classification Search
  CPC . G06T 7/001; G06T 7/62; G06T 2207/30136; B22D 43/007; B22D 37/00; F27D 21/00; F27D 21/02; C21B 3/04; Y02W 30/542
  See application file for complete search history.

(56) References Cited

U.S. PATENT DOCUMENTS

| | | | | |
|---|---|---|---|---|
| 5,694,480 | A * | 12/1997 | Itakura | C21B 3/08 |
| | | | | 382/141 |
| 5,968,227 | A * | 10/1999 | Goldstein | B22D 2/001 |
| | | | | 75/375 |
| 6,130,637 | A * | 10/2000 | Meszaros | C21C 5/4673 |
| | | | | 342/123 |
| 6,197,086 | B1 * | 3/2001 | Stofanak | B22D 2/001 |
| | | | | 266/93 |
| 6,255,983 | B1 | 7/2001 | Meszaros et al. | |
| 6,562,285 | B1 * | 5/2003 | Demysh | C21C 5/4673 |
| | | | | 266/100 |
| 2003/0004602 | A1 | 1/2003 | Koffron et al. | |
| 2007/0119275 | A1 * | 5/2007 | Kemeny | C21C 5/5211 |
| | | | | 75/10.12 |
| 2012/0167543 | A1 * | 7/2012 | Iida | F23J 1/00 |
| | | | | 60/39.12 |
| 2014/0208896 | A1 * | 7/2014 | Tupkary | C21B 3/10 |
| | | | | 75/414 |
| 2015/0192365 | A1 * | 7/2015 | Koubek | F27D 21/02 |
| | | | | 348/83 |
| 2016/0148365 | A1 * | 5/2016 | Tsuda | F27D 1/16 |
| | | | | 382/141 |

FOREIGN PATENT DOCUMENTS

| | | |
|---|---|---|
| CN | 1538889 A | 10/2004 |
| CN | 102183288 B | 1/2013 |
| CN | 105160683 A | 12/2015 |
| JP | 2002-523753 A | 7/2002 |
| JP | 2003-13129 A | 1/2003 |
| JP | 2003-19553 A | 1/2003 |
| JP | 2004-144652 A | 5/2004 |
| JP | 2007-119837 A | 5/2007 |
| JP | 2013-160627 A | 8/2013 |

OTHER PUBLICATIONS

Office Action for TW 106142738 dated Jul. 31, 2018.
Written Opinion of the International Searching Authority for PCT/JP2017/043809 (PCT/ISA/237) dated Mar. 6, 2018.
Sugiura et al., "Continuous Temperature Measurement of Liquid Iron and Slag Tapped from a Blast Furnace", SICE Journal of Control, Measurement, and System Integration, vol. 7, No. 3, May 1, 2014, pp. 147-151, XP055705443, ISSN: 1882-4889.

* cited by examiner

SLAG VOLUME EVALUATION METHOD FOR MOLTEN METAL SURFACE

TECHNICAL FIELD OF THE INVENTION

The present invention relates to a slag volume evaluation method for a molten metal surface.

Priority is claimed on Japanese Patent Application No. 2016-236936, filed on Dec. 6, 2016, the content of which is incorporated herein by reference.

RELATED ART

Slag floats on a surface of a molten metal, such as a molten iron taken out to a molten iron ladle from a blast furnace or a molten steel taken out to a ladle from a converter furnace, contained in a container. There is concern that slag floating on a surface of the molten iron contained in the molten iron ladle will cause component deviation in a converter furnace process which is a post-process. In addition, there is concern that slag floating on a surface of the molten steel contained in the ladle will also cause component deviation in a secondary refining process which is a post-process. In this manner, there is concern that slag floating on the surface of the molten metal contained in the container will harmfully affect the post-process. Therefore, a slag scraping operation for removing slag is generally performed using a slag scraping apparatus configured to scrape off slag from the container before the molten metal is sent to the post-process.

In accordance with the kind or the like of a molten metal, there are a case where a slag scraping operation for perfectly removing slag from a container is required to be performed (perfect slag scraping) and a case where a slag scraping operation for partially removing slag is favorably performed such that a part of the slag remains in a container (partial slag scraping). When slag is scraped off, not only slag but also a molten metal is partially scraped off. Therefore, generally, when the amount of scraped slag increases, the amount of a scraped molten metal also increases. Therefore, the partial slag scraping has an advantage capable of reducing a loss in molten metal and enhancing the yield, compared to the perfect slag scraping. However, in the case of partial slag scraping, if slag remains in a container more than necessary, there is concern that the slag will harmfully affect a post-process as described above. Therefore, it is necessary to accurately grasp the amount of slag remaining in a container by obtaining a slag scraping rate, for example.

Here, as a technology in the related art, there is a method of obtaining a slag scraping rate from a slag area in the case where a container is viewed from above. However, when a part of slag in a container is scraped off, there are cases where a phenomenon in which an upper portion of the remaining slag collapses and falls down onto a molten metal surface such that the slag seems to spread on the molten metal surface occurs, for example. In this case, if the slag scraping rate is obtained by the method of the technology in the related art, even though slag is scraped off, the slag scraping rate does not increase, as a result. That is, there are many cases where the slag area and the slag scraping rate are not correlated to each other. Accordingly, it is difficult to accurately grasp the amount of slag remaining in a container by the method of the technology in the related art.

In addition, Patent Document 1 discloses a method of discriminating between slag and a molten metal by obtaining a luminance histogram from image data obtained by capturing an image of a molten metal surface in a molten metal container using an image capturing device installed in the vicinity of the molten metal container, determining the stage of slag scraping, among an early stage, an intermediate stage, and a later stage, from a pattern of this luminance histogram, obtaining a slag determination threshold value from a luminance histogram peak position in each of these stages, and binarizing the luminance according to the set threshold value.

According to the method of Patent Document 1, it is assumed that slag and a molten metal can be accurately discriminated, compared to the case where the threshold value for discriminating between slag and a molten metal is fixed. Therefore, according to the method of Patent Document 1, it is assumed that the amount of slag on a molten metal surface can be accurately calculated to a certain degree.

However, real slag has a thickness, and it is assumed that the thickness of slag gradually decreases in a process of the slag scraping operation. Particularly, in the case of partial slag scraping, it is necessary to accurately grasp the amount of slag remaining in a container. However, in the method of Patent Document 1, since the thickness of slag is not evaluated, it is difficult to accurately grasp the amount of slag remaining in a container. In addition, in the method of Patent Document 1, many processes are required to calculate the amount of the slag, so that it is difficult to promptly grasp the amount of the slag.

PRIOR ART DOCUMENT

Patent Document

[Patent Document 1] Japanese Unexamined Patent Application, First Publication No. 2003-19553

DISCLOSURE OF THE INVENTION

Problems to be Solved by the Invention

The present invention has been made in consideration of the foregoing circumstances, and an object thereof is to provide a slag volume evaluation method for a molten metal surface, in which the volume of slag floating on the surface of the molten metal in the container can be evaluated more accurately and more promptly.

Means for Solving the Problem

The inventors have focused on that slag, which floats on a surface of a molten metal in a container and is cooled and solidified by being exposed to the atmosphere, absorbs radiation heat radiated from the molten metal through heat radiation, and the absorption degree of radiation heat varies in accordance with the thickness of slag. Then, the inventors have found that when an image of a molten metal surface is captured in a state where a plurality of pieces of slag differing from each other in thickness float on a surface of a molten metal, and when the relationship between the thickness and the density (luminance) of the slag are calculated in advance, the volume of the slag can be calculated according to the captured image of the molten metal surface which is an evaluation target.

In order to solve the foregoing problem, the present invention employs the following aspects according to the knowledge described above.

(1) According to an aspect of the present invention, there is provided a slag volume evaluation method for a molten metal surface, in which a volume of slag floating on a surface of a molten metal contained in a container is evaluated according to a captured image of a molten metal surface in the container. The slag volume evaluation method includes calculating an approximation curve indicating a correspondence between a thickness of the slag and a density parameter in advance by measuring thicknesses of a plurality of pieces of the slag which float on the surface of the molten metal and differ from each other in thickness, and calculating a value of the density parameter which is correlated to a density in a pixel region corresponding to the plurality of pieces of the slag in the captured image obtained by capturing an image of the molten metal surface in the container in a state where the plurality of pieces of the slag are floating on the surface of the molten metal; capturing the image of the molten metal surface which is an evaluation target; and calculating the volume of the slag by calculating the thickness of the slag for each of pixels constituting the captured image obtained through the capturing, and integrating the calculated thickness of the slag for each of the pixels, according to the value of the density parameter of each of the pixels constituting the captured image obtained through the capturing and the approximation curve calculated through the calculating of the approximation curve.

(2) The aspect according to (1) may be constituted as follows: the slag volume evaluation method may further include scraping off the slag from the container; and calculating a residual ratio of the slag in the container. In the capturing, images of the molten metal surface in the container before the scraping and the molten metal surface in the container after the scraping are captured. In the calculating of the volume of the slag, the volume of the slag in the container before the scraping and the volume of the slag in the container after the scraping are calculated. In the calculating of the residual ratio of the slag, the residual ratio of the slag in the container is calculated by dividing the volume of the slag in the container after the scraping by the volume of the slag in the container before the scraping.

Effects of the Invention

According to each of the foregoing aspects of the present invention, the volume of the slag floating on the surface of the molten metal in the container can be evaluated more accurately and more promptly.

EMBODIMENT OF THE INVENTION

Hereinafter, with reference to the drawings, a slag volume evaluation method for a molten metal surface (which will hereinafter be simply referred to as a "slag volume evaluation method" as well) according to an embodiment of the present invention will be described. In this specification and the drawings, the same reference signs are applied to constituent elements having substantially the same functional configuration, and duplicated description thereof will be omitted.

First, a configuration of a slag volume evaluation apparatus used in the slag volume evaluation method according to the present embodiment will be described.

Figure 1:
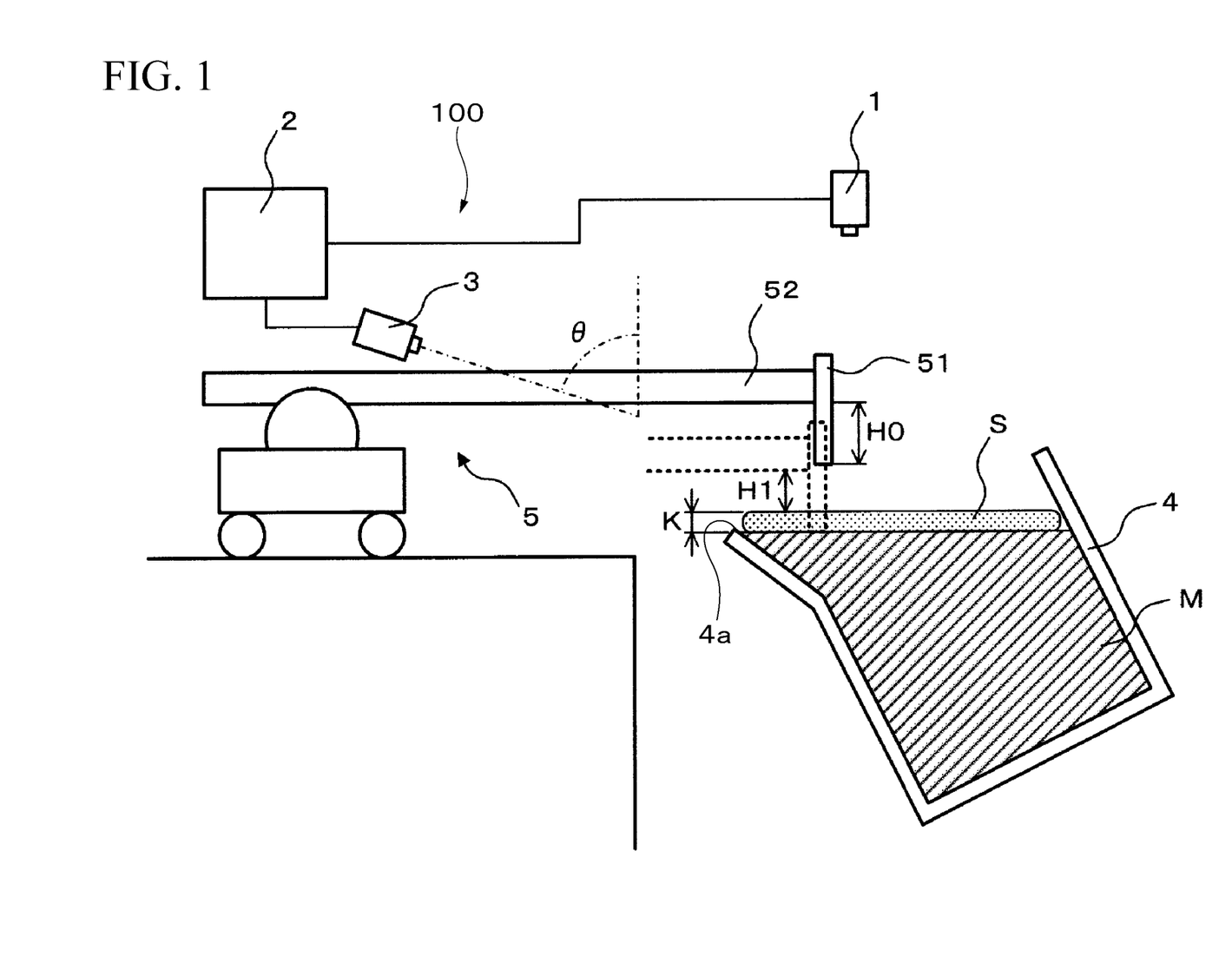
FIG. 1 is a schematic view showing a schematic configuration of a slag volume evaluation apparatus used in a slag volume evaluation method according to an embodiment of the present invention.

FIG. 1 is a schematic view showing a schematic configuration of a slag volume evaluation apparatus 100 used in the slag volume evaluation method according to the present embodiment. FIG. 1 shows a cross section of a container 4 containing a molten metal M.

As shown in FIG. 1, the slag volume evaluation apparatus 100 is used in a slag scraping operation of scraping off slag S floating on a surface of the molten metal M such as a molten iron, which is contained in the container 4 such as a tilted molten iron ladle, from the container 4 by using a slag scraping apparatus 5 having a scraping plate 51 and an arm 52.

The temperature of the molten metal M contained in the container 4 is within a range of 1,200° C. to 1,400° C., for example, and the molten metal M emits light due to heat radiation (that is, the molten metal M is self-illuminating due to heat radiation). On the other hand, the slag S floating on the surface of the molten metal M contained in the container 4 is cooled by being exposed to the atmosphere and a part near the surface is solidified, so that it is not substantially self-illuminating and is shielding the molten metal from emitting light.

The slag volume evaluation apparatus 100 includes a first image capturing unit 1 that captures an image of a molten metal surface in the container 4 from above in a vertical direction, a second image capturing unit 3 that captures an image of a molten metal surface in the container 4 from above oblique to the vertical direction, and an image processor 2 that is connected to the first image capturing unit 1 and the second image capturing unit 3.

In this specification, a "molten metal surface" means not only a surface of the molten metal M but also means a surface of slag in a case where slag is floating on the surface of a molten metal. That is, it means the outermost surface (uppermost surface) of the contents in the container 4.

For example, a CCD camera having main sensitivity in a visible light region or a thermal imaging camera (thermography) having main sensitivity in an infrared light region can be used as the first image capturing unit 1. In the present embodiment, a CCD camera is used as the first image capturing unit 1.

In the case of using a CCD camera as in the present embodiment, a value of the density in a pixel region corresponding to slag in a captured image can be calculated. In addition, in the case of using a thermal imaging camera (thermography), a value of the temperature or the density (density before being converted into a temperature) in the pixel region can be calculated.

For example, the image processor 2 is constituted of a general purpose personal computer in which a predetermined program for executing a slag volume calculating step ST3 and a slag residual ratio calculating step ST7 (which will be described below) is installed. The image processor 2 has a monitor for displaying captured images obtained by the first image capturing unit 1 and the second image capturing unit 3.

Similar to the first image capturing unit 1, for example, a CCD camera having main sensitivity in a visible light region or a thermal imaging camera (thermography) having main sensitivity in an infrared light region can be used as the second image capturing unit 3. In the present embodiment, a CCD camera is used as the second image capturing unit 3.

The slag volume evaluation method according to the present embodiment is executed by using the slag volume evaluation apparatus 100. Hereinafter, the slag volume evaluation method according to the present embodiment will be described.

Figure 2:
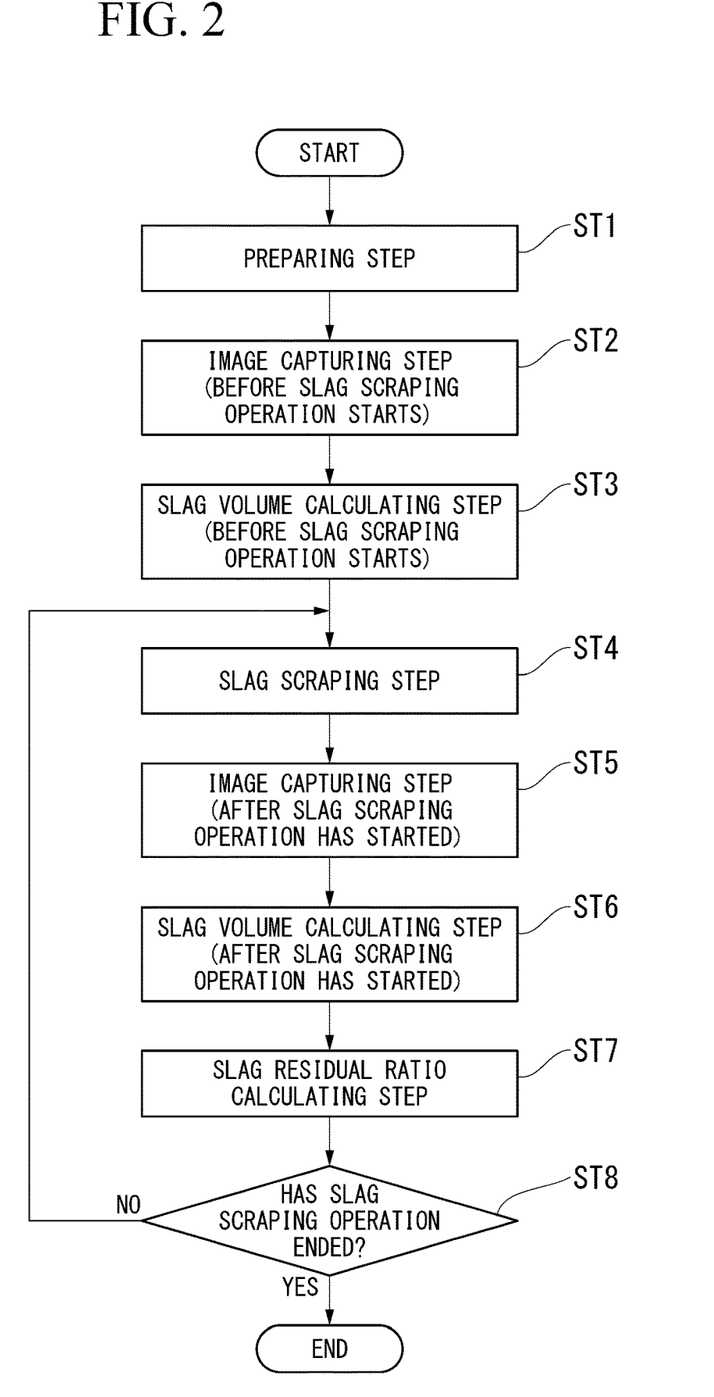
FIG. 2 is a flowchart showing the slag volume evaluation method.

FIG. 2 is a flowchart showing the slag volume evaluation method according to the present embodiment. The slag volume evaluation method according to the present embodiment is a method of evaluating the volume of the slag S floating on the surface of the molten metal M according to a captured image obtained by the first image capturing unit 1 capturing an image of a molten metal surface in the container 4 containing the molten metal M. As shown in FIG. 2, The slag volume evaluation method has a preparing step ST1, an image capturing step ST2, the slag volume calculating step ST3, a slag scraping step ST4, an image capturing step ST5, a slag volume calculating step ST6, the slag residual ratio calculating step ST7, and a determining step ST8 of determining whether or not to end slag scraping operations.

Hereinafter, details of each of the steps will be sequentially described.

(Preparing Step ST1)

In the preparing step ST1, first, an image of a molten metal surface in a state where a plurality of pieces of the slag S differing from each other in thickness are simultaneously floating on the surface of the molten metal M is captured by using the first image capturing unit 1. At this time, images of a plurality of molten metal surfaces obtained in different stages of slag scraping operation (partial slag scraping) using the slag scraping apparatus 5 may be captured. Alternatively, an image of a single molten metal surface at a certain point of time during slag scraping operation may be captured. Specific examples of a plurality of molten metal surfaces which can be obtained in different stages of slag scraping operation (partial slag scraping) can include a molten metal surface before slag scraping operation of the slag S starts (molten metal surface assumed to have the thickest slag S), a molten metal surface in an intermediate stage of slag scraping operation, and a molten metal surface after slag scraping operation ends (molten metal surface assumed to have the thinnest slag S), for example.

Captured images are stored in the image processor 2.

The diaphragm of a lens provided in the first image capturing unit 1, and the gain of a video signal output from the first image capturing unit 1 are adjusted such that the density in the pixel region corresponding to the molten metal M in a captured image obtained by the first image capturing unit 1 becomes 255 (white), that is, the absolute maximum value. A similar configuration applies to the image capturing step ST2, which will be described below.

In addition, in the present embodiment, the visual field of the first image capturing unit 1 is set such that not only the molten metal surface of the container 4 but also the container 4 and a background B are included within the visual field. The visual field of the first image capturing unit 1 may be set such that only the molten metal surface of the container 4 is included within the visual field.

Here, for example, a "density" in this specification indicates light and shade of an image (that is, luminance of an image) of 256 tones. The relationship between this density and the heat radiation luminance on a molten metal surface in a container is a linear relationship.

Figure 3:
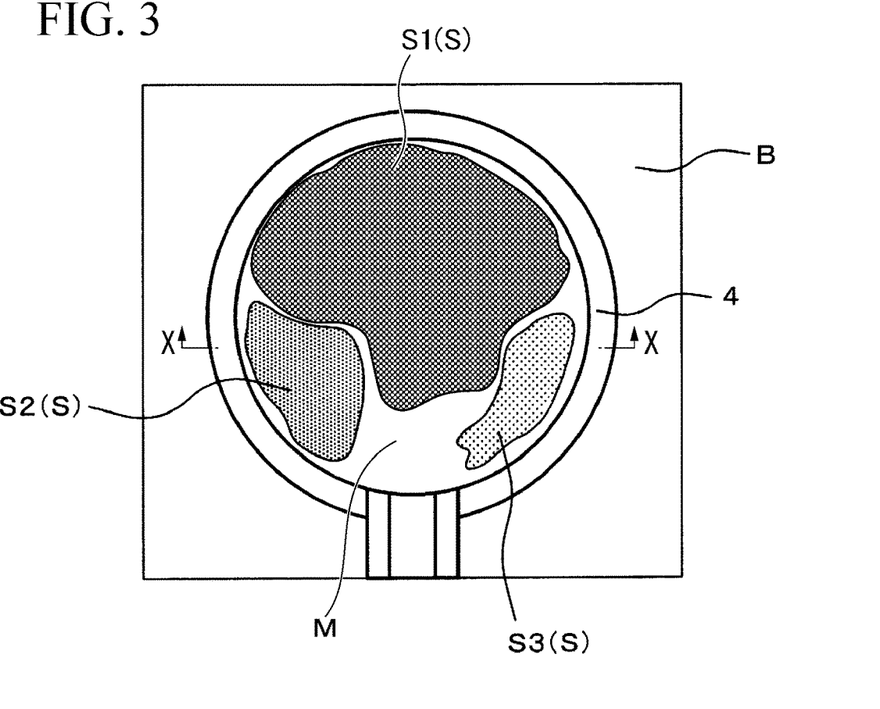
FIG. 3 is a view showing an example of a captured image obtained by capturing an image of a molten metal surface in a container using a first image capturing unit 1 shown in FIG. 1.

FIG. 3 is a view schematically showing an example of a captured image obtained by capturing an image of a molten metal surface in the container 4 using the first image capturing unit 1. FIG. 3 shows a case where the visual field of the first image capturing unit is set to a wide visual field in which the container 4 and the background B are included within the visual field, and a plurality of pieces of the slag S1 to S3 differing from each other in thickness are simultaneously floating on a single molten metal surface. In FIG. 3, the slag S1 has the largest thickness, and the thickness decreases in the order of the slag S2 and the slag S3.

In the captured image shown in FIG. 3, in pixel regions corresponding to the pieces of slag S, a pixel region corresponding to the thickest slag S1 becomes the darkest (low density), and a pixel region corresponding to the thinnest S3 becomes the brightest (high density). In addition, as described above, the density in the pixel region corresponding to the molten metal M is 255 (white), that is, the absolute maximum value.

Since the temperatures of the container 4 and the background B are lower than those of the molten metal M and the slag S, the pixel region corresponding to the container 4 and the pixel region corresponding to the background B actually become dark (low density). However, for the convenience of illustration, they are indicated with white similar to the pixel region corresponding to the molten metal M.

Figure 4:
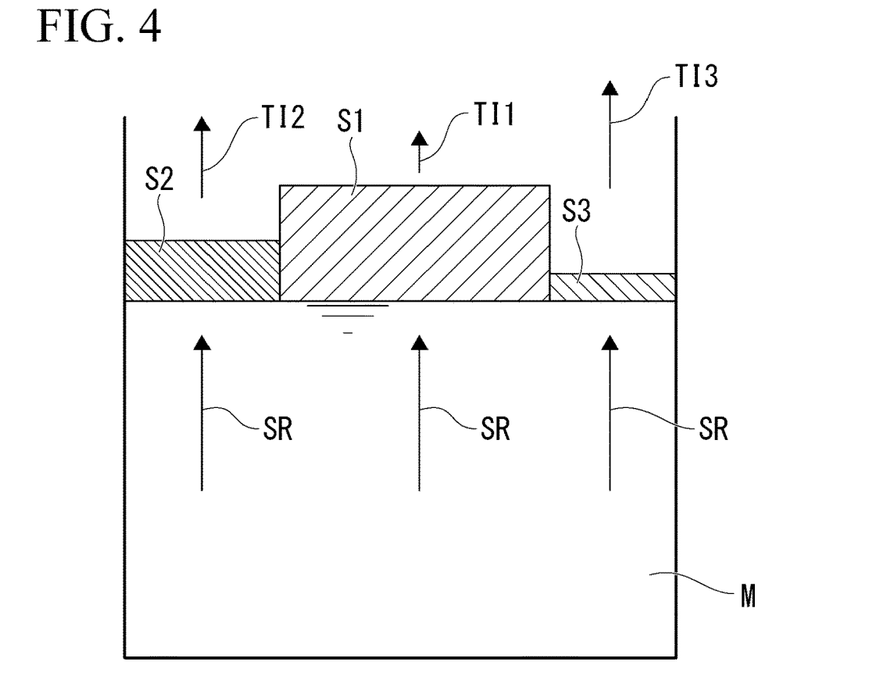
FIG. 4 is a view showing a state where slag S1 to slag S3 shown in FIG. 3 are floating on the molten metal surface in the container and is a cross-sectional view taken along line X-X in FIG. 3.

Here, using FIG. 4, a reason that the pixel regions respectively corresponding to the slag S1 to the slag S3 shown in FIG. 3 differ from each other in brightness will be described. FIG. 4 is a view showing a state where the slag S1 to the slag S3 are floating on the molten metal M in the container 4 and is a cross-sectional view taken along line X-X in FIG. 3.

As shown in FIG. 4, a part of radiation light SR radiated from the molten metal M due to heat radiation is absorbed into the slag S1 to the slag S3. On the other hand, the radiation light SR which has been transmitted through the slag S1 to the slag S3 becomes transmitted light TI1 to transmitted light TI3, and the transmitted light TI1 to the transmitted light TI3 are incident on the first image capturing unit 1.

When the thickness of slag increases, the slag absorbs more radiation light SR. Therefore, the intensity of light increases in the order of the transmitted light TI1 transmitted through the slag S1, the transmitted light TI2 transmitted through the slag S2, and the transmitted light TI3 transmitted through the slag S3. Accordingly, in the captured image shown in FIG. 3, the pixel region becomes brighter in the order of the slag S1, the slag S2, and the slag S3.

Subsequently, in the preparing step ST1, the value of a density parameter correlated to the density in a pixel region corresponding to the slag S1 to the slag S3 in the captured image shown in FIG. 3 is calculated. Regarding the density parameter, the temperature can be included as an example, in addition to the density itself. However, in the present embodiment, the density itself is used as a density parameter.

Specifically, the average density for the pixel regions corresponding to the slag S1 to the slag S3 is calculated. For example, the pixel regions corresponding to the slag S1 to the slag S3 can be recognized by an operator causing the monitor of the image processor 2 to display a captured image and visually recognizing the image. For example, if a program of calculating the average density or the like within the contour designated by using a pointing device such as a mouse is installed in the image processor 2, the image processor 2 can automatically calculate the average density for the pixel regions corresponding to the slag S1 to the slag S3 when the operator designates the contour of each piece of the slag S1 to the slag S3 while visually recognizing the monitor.

Thereafter, in the preparing step ST1, an approximation curve indicating the correspondence between the thickness and the density of the slag S is calculated by using the value of the average density for the pixel regions corresponding to the slag S1 to the slag S3. In other words, an approximation curve is calculated by applying a least-squares method, for example, using the values of the thicknesses of a plurality of pieces of the slag S (in the example shown in FIG. 3, the slag S1 to the slag S3) differing from each other in thickness and the average density for the pixel regions corresponding to the pieces of slag S. In the present embodiment, as a preferable aspect, an approximation curve is calculated by not only using the values of the densities in the pixel regions corresponding to the pieces of slag S but also using the value of the density (255, in the present embodiment) in the pixel region in which the thickness of the slag S is zero (that is, the pixel region corresponding to the molten metal M).

The thickness of each piece of slag S can be measured by comparing the dimension of the scraping plate 51 of the slag scraping apparatus 5 in the vertical direction with the slag S, for example. Specifically, in the present embodiment, as shown in FIG. 1, a lower surface of the scraping plate 51 is caused to substantially coincide with a lower surface of the slag S (upper surface of the molten metal M) by driving (turning) the arm 52 of the slag scraping apparatus 5 such that a lower end portion of the scraping plate 51 to be buried in the slag S. Then, an image of a molten metal surface in the container 4 is captured by the second image capturing unit 3 from above oblique to the vertical direction. Accordingly, a captured image in which both the slag S and the scraping plate 51 are photographed can be obtained.

As shown in FIG. 1, in a state where the container 4 is tilted, positions of the upper surface of the molten metal M and a spout 4a of the container 4 in the height direction substantially coincide with each other. Therefore, the lower surface of the scraping plate 51 can substantially coincide with the lower surface of the slag S (upper surface of the molten metal M) by causing the height position of the spout 4a and the height position of the lower surface of the scraping plate 51 to substantially coincide with each other. In addition, the scraping plate 51 may be lowered by calculating the position of the molten metal surface in advance when the container 4 is tilted, according to the volume of the molten metal M in the container 4, such that the calculated position of the molten metal surface and the lower surface of the scraping plate 51 substantially coincide with each other.

Thereafter, when the monitor of the image processor 2 displays this captured image and an operator visually recognizes this, a distance H1 between a lower surface of the arm 52 and an upper surface of the slag S is calculated. Specifically, for example, when a program for calculating a distance (actual dimension) of a straight line, which passes two points designated by using a pointing device such as a mouse, through geometric computation using the image capturing magnification and the visual-line angle (θ shown in FIG. 1) of the second image capturing unit 3 set in advance is installed in the image processor 2, the image processor 2 can automatically calculate the distance H1 by designating two points between the lower surface of the arm 52 and the upper surface of the slag S while an operator visually recognizes the monitor. Since a distance H0 between the lower surface of the arm 52 and the lower surface of the scraping plate 51 is ascertained in advance, a thickness K of the slag S at a position where the lower end portion of the scraping plate 51 is buried can be calculated by subtracting the distance H1 from the distance H0 using the relational expression K=H0−H1.

In the example shown in FIG. 3, the foregoing procedure is executed by sequentially burying the lower end portion of the scraping plate 51 in each piece of the slag S1 to the slag S3, and the thickness of each piece of the slag S1 to the slag S3 is measured.

In the present embodiment, in order to accurately approximate the correspondence between the thickness K and a density I of slag, the approximation curve to be calculated is expressed by an exponential function. Specifically, when the thickness of slag is K and the value of the density is I, the approximation curve expressed by the following Expression (1) is calculated (coefficient a is identified by a least-squares method or the like).

$$I=I_0 \times e^{-aK} \quad (1)$$

In the foregoing Expression (1), $I_0$ means the value of the density in the pixel region corresponding to the molten metal M (255, in the present embodiment) in a captured image obtained in the preparing step ST1, e means a base of a natural logarithm, and a means a positive coefficient, respectively.

Figure 5:
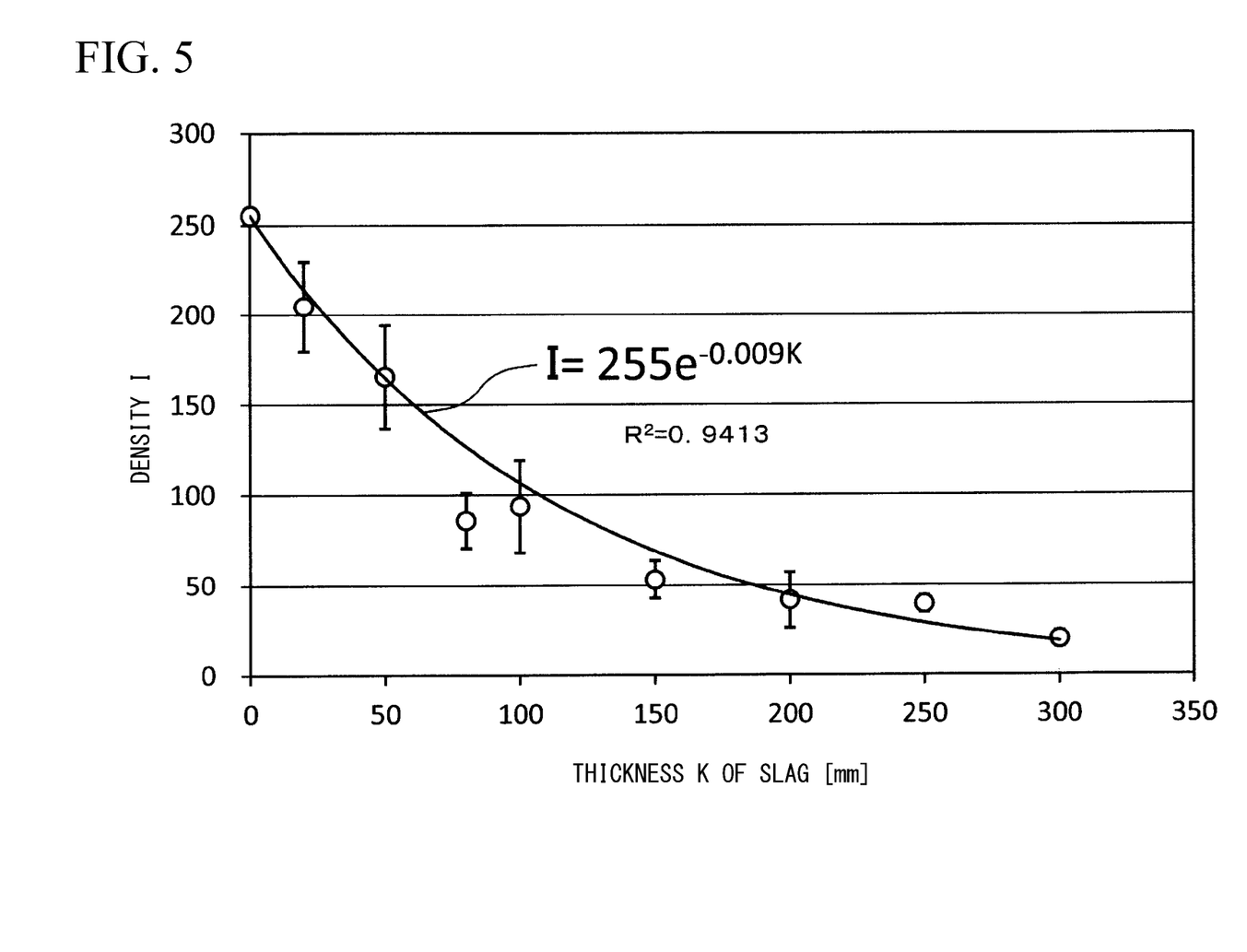
FIG. 5 is a view showing an example of an approximation curve calculated in a preparing step ST1 shown in FIG. 2.

FIG. 5 is a view showing an example of an approximation curve calculated in the preparing step ST1. Data circularly plotted in FIG. 5 indicates the density I in the thickness K of the slag S used in calculating an approximation curve, and a vertically extending bar indicates a fluctuation (standard deviation 1σ) in the density of the same thickness K. In FIG. 5, when the coefficient a=0.009 is obtained for the foregoing Expression (1) and the correlation coefficient between the thickness K and the density I of the slag S is R, $R^2=0.9413$ is established, so that it is ascertained that the thickness K and the density I can be approximated in a relatively accurate manner.

The preparing step ST1 described above is executed before evaluating the volume of the slag S on the molten metal surface which will actually become an evaluation target. Then, the correspondence (approximation curve) between the thickness K and the density I of the slag S obtained in the preparing step ST1 is stored in the image processor 2, thereby being used in the slag volume calculating step ST3, which will be described below. Specifically, the following Expression (2) is stored in the image processor 2.

(Image Capturing Step ST2)

Next, in the image capturing step ST2, the first image capturing unit 1 captures an image of the molten metal surface which will become an evaluation target. At this time, image capturing conditions such as the diaphragm of the lens provided in the first image capturing unit 1 and the gain of a video signal output from the first image capturing unit 1 are the same as the conditions set in the preparing step ST1.

(Slag Volume Calculating Step ST3)

In the slag volume calculating step ST3, the image processor 2 calculates the thickness K of the slag S for each of pixels constituting a captured image obtained in the image capturing step ST2 according to the value of the density I of each of the pixels constituting the captured image obtained in the image capturing step ST2, and the approximation curve calculated in the preparing step ST1. At this time, since the calculated thickness K of the slag S is adopted as the function of the density I, the following Expression (2) obtained by modifying the foregoing Expression (1) is used. The factor "ln" in the following Expression (2) means a natural logarithm.

$$K(I)=(-1/a)\times \ln(I/I_0) \qquad (2)$$

As described above, the coefficient a is obtained in the preparing step ST1 in advance (in the example shown in FIG. 5, a=0.009). The density $I_0$ is also set in the preparing step ST1 in advance (in the example shown in FIG. 5, $I_0$=255). The coefficient a and the density $I_0$ are stored in the image processor 2. Therefore, the image processor 2 can automatically calculate the thickness K of the slag S corresponding to this density I by substituting the value of the density I of each of the pixels in the foregoing Expression (2).

Figure 6A:
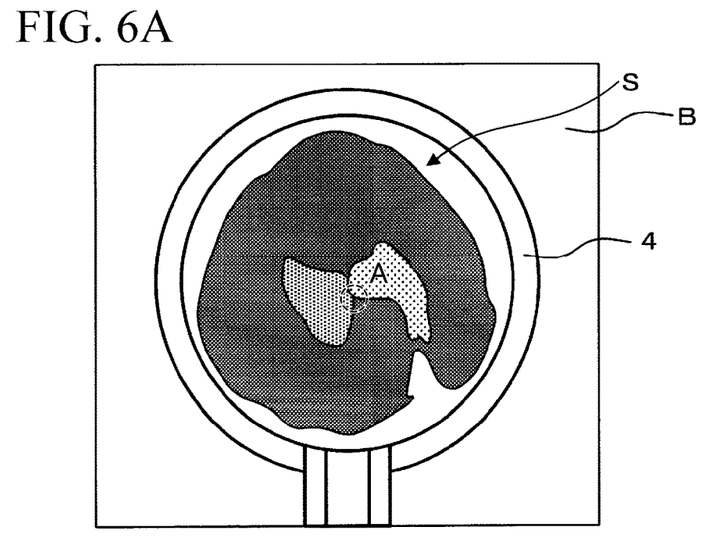
FIG. 6A is a view showing a procedure of calculating a thickness of slag in a slag volume calculating step ST3 shown in FIG. 2 and is a view showing an example of a captured image obtained in an image capturing step ST2.
Figure 6B:
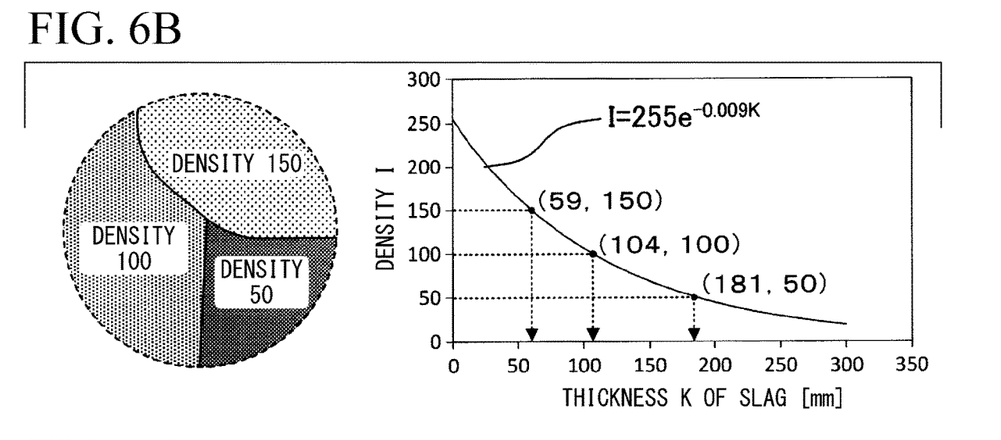
FIG. 6B is a view showing the procedure of calculating the thickness of slag in the slag volume calculating step ST3 shown in FIG. 2 and is an enlarged view of a pixel region surrounded by a dotted line A in FIG. 6A.
Figure 6C:
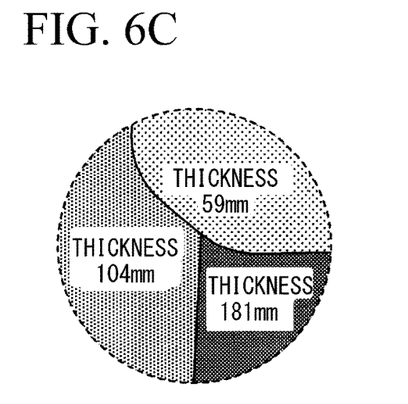
FIG. 6C is a view showing the procedure of calculating a thickness of slag in the slag volume calculating step ST3 shown in FIG. 2 and is a view showing the calculated thicknesses of the slag in the pixel regions shown in FIG. 6B.

FIGS. 6A to 6C are views showing a procedure of calculating the thickness K of the slag S in the slag volume calculating step ST3. FIG. 6A is a view schematically showing an example of a captured image obtained in the image capturing step ST2. FIG. 6B is an enlarged view (diagram on the left) of a pixel region surrounded by a dotted line A in FIG. 6A, and is a graph (diagram on the right) for calculating the thickness of slag from the density in the pixel region using the approximation curve shown in FIG. 5. FIG. 6C is a view showing the calculated thickness K of the slag S in the pixel region shown in FIG. 6B.

If pixel regions having densities of 50, 100, and 150 are present in the pixel region surrounded by the dotted line A in FIG. 6A, thicknesses of 181 mm, 104 mm, and 59 mm are calculated according to the approximation curve shown in FIG. 6B (according to the foregoing Expression (2)).

In the slag volume calculating step ST3, the foregoing processing described in regard to the pixel region surrounded by the dotted line A is executed for each of the pixels constituting the captured image obtained in the image capturing step ST2.

However, as shown in FIG. 6A, in a case where pixel regions corresponding to the container 4 and the background B are present in the captured image, the densities in these pixel regions are low as described above, the thicknesses to be calculated according to the approximation curve increase. Therefore, if the thicknesses of these pixel regions are added to integration (which will be described below), a significant error occurs in the calculated volume of the slag S.

Therefore, for example, among all of the pixels constituting the captured image, only the pixels positioned on an inner side of the pixel region corresponding to the container 4 are adopted as a target for calculating the thickness. Generally, there are many cases where the position of the container 4 when performing the slag scraping operation is fixed. In these cases, the positions of the pixel regions corresponding to the container 4 and the background B in the captured image do not fluctuate. Therefore, the thicknesses of only the pixels positioned on an inner side of the pixel region can be calculated by setting and storing the coordinates of the pixels positioned on an inner side of the pixel region corresponding to the container 4 in the captured image in the image processor 2 in advance.

In addition, for example, only the thicknesses of the pixels positioned on an inner side of the pixel region corresponding to the container 4 may be integrated after the thicknesses of all of the pixels constituting the captured image (also including the pixels corresponding to the container 4 and the background B) are calculated.

In addition, generally, the densities in the pixel regions corresponding to the container 4 and the background B are lower than the densities in the pixel regions corresponding to the molten metal M and the slag S. Therefore, for example, only the pixels having a density with a predetermined threshold value or higher may be adopted as a target.

In addition, only the thicknesses of the pixels having a density with the predetermined threshold value or higher may be integrated after the thicknesses of all of the pixels constituting the captured image are calculated. The predetermined threshold value is a value which can discriminate between the densities in the pixel regions corresponding to the molten metal M and the slag S and the densities in the pixel regions corresponding to the container 4 and the background B.

In addition, for example, the visual field of the first image capturing unit 1 may be adjusted in advance such that only an image of the molten metal surface in the container 4 is captured. However, if the visual field is excessively small, there is concern that a part of the slag S will be out of the visual field, so that the volume of the slag S cannot be accurately calculated. Therefore, it is preferable that the visual field is adjusted as large as a range in which the container 4 is not photographed.

The pixel region corresponding to the molten metal M may be or not be adopted as the calculation target. Since the density in the pixel region corresponding to the molten metal M is $I_0$ (255, in the present embodiment), the thickness K ($I_0$) calculated in the foregoing Expression (2) becomes zero. Therefore, even if the thickness of the pixel region corresponding to the molten metal M is calculated and the value thereof is added to the integration (which will be described below), and no error occurs in the volume of the slag S to be calculated.

Subsequently, in the slag volume calculating step ST3, the volume of the slag S is calculated by integrating the calculated thickness for each of the pixels.

Specifically, regarding a captured image captured at a time t having the starting time of the slag scraping operation as a starting point, when the total number of pixels of the density I is Ns (t, I), the image processor 2 calculates a volume V(t) of the slag S at the time t according to the following Expression (3), for example. In the following Expression (3), $I_{th}$ means the predetermined threshold value described above, which can discriminate between the densities in the pixel regions corresponding to the molten metal M and the slag S and the densities in the pixel regions corresponding to the container 4 and the background B. The unit of the volume calculated in the following Expression (3) is pixel×pixel×thickness (mm). However, if resolution (actual dimensions) per pixel is obtained in advance according to the image capturing magnification or the like of the first image capturing unit 1, the volume can be calculated at the unit of actual dimensions.

[Math 1]

$$V(t) = \sum_{I=Ith}^{I_0} K(I) \cdot Ns(t, I) \tag{3}$$

(Slag Scraping Step ST4)

Next, in a state where the container 4 is tilted, a part of the slag S is scraped off from the container 4 by using the slag scraping apparatus 5 (refer to FIG. 1). That is, in the slag scraping step ST4, a slag scraping operation is performed without scraping off all of the pieces of slag in the container 4 such that a part of the slag S remains in the container 4.

(Image Capturing Step ST5)

In the image capturing step ST5, an image of the molten metal surface in the container 4 after the slag scraping step ST4 is captured. The image capturing conditions and the like are similar to those in the image capturing step ST2.

(Slag Volume Calculating Step ST6)

In the slag volume calculating step ST6, the volume of slag in the container 4 after the slag scraping step ST4 is calculated according to the captured image obtained in the image capturing step ST5. A calculation method is similar to that in the slag volume calculating step ST3 described above.

(Slag Residual Ratio Calculating Step ST7)

In the slag residual ratio calculating step ST7, the residual ratio of the slag S in the container 4 is calculated by dividing the volume of the slag S, which is calculated by the image processor 2 in the slag volume calculating step ST6 (volume of the slag S calculated according to the captured image captured after the slag scraping step ST4), by the volume of the slag S calculated in the slag volume calculating step ST3 (volume of the slag S calculated according to the captured image captured before the slag scraping step ST4). That is, the image processor 2 calculates a residual ratio Ps(t) of the slag S at the time t according to the following Expression (4). The calculated residual ratio Ps(t) of the slag S is stored in the image processor 2 and is displayed in the monitor.

$$Ps(t)=V(t)/V(0) \tag{4}$$

A slag scraping rate Qs(t) of the slag S can be calculated by the following Expression (5) using the residual ratio Ps(t) of the slag S.

$$Qs(t)=1-Ps(t) \tag{5}$$

Next, an operator visually recognizes the residual ratio Ps(t) of the slag S displayed in the monitor, determines whether or not it has arrived a desired residual ratio, and decides whether or not to end the slag scraping operation of the slag S (ST8 of FIG. 2). In a case of ending the slag scraping operation (in a case of "Yes" in ST8 of FIG. 2), the slag volume evaluation method according to the present embodiment is completed.

On the other hand, in a case of not ending the slag scraping operation (in a case of "No" in ST8 of FIG. 2), the slag scraping step ST4, the image capturing step ST5, the slag volume calculating step ST6, and the slag residual ratio calculating step ST7 are repetitively executed.

According to the slag volume evaluation method of the present embodiment described above, in the preparing step ST1, an approximation curve indicating the correspondence between the thickness and the density of the slag S is calculated in advance, and the thickness of slag is calculated for each of the pixels constituting a captured image of a molten metal surface which is obtained in the image capturing step ST2 according to this approximation curve and will become an evaluation target. Accordingly, the volume of the slag S can be evaluated more accurately and promptly. Therefore, in the process of the slag scraping operation of the slag S, the slag scraping operation can be optimized by successively evaluating the volume of the slag S remaining in the container 4 such that the slag S does not remain in the container 4 more than necessary.

In addition, according to the slag volume evaluation method of the present embodiment, the residual ratio of the slag S in the container 4 is calculated in the slag residual ratio calculating step ST7. If this residual ratio is used, when the molten metal M in the container 4 is processed in a post-process, the amount of a sulfur component included in this molten metal M can be estimated. Accordingly, adjustment of the component in the molten metal M in the post-process can be optimized.

Here, as an example of refining in which a sulfur component in a molten metal in a container is desulfurized by adding a desulfurizing agent (flux) and the sulfur component in the molten metal is transferred to generated slag, it is generally known that the residual ratio of the slag in the container is correlated to the sulfur component content in the molten metal in the post-process.

In a pre-process of the slag scraping operation, if sample analysis is used, the content rate of a sulfur component in a molten metal before slag is generated and the content rate of a sulfur component in the molten metal after slag is generated (after desulfurization refining) can be measured, so that the sulfur component content in the slag in the container before the slag scraping operation starts can be calculated according to both measurement results (difference between content rates×amount of molten metal=sulfur component content in slag).

According to the present embodiment, the residual ratio of slag in the container 4 can be calculated in the slag residual ratio calculating step ST7. Therefore, the sulfur component content in slag in a container after the slag scraping operation has started can be calculated according to the calculate residual ratio of the slag and the sulfur component content in the slag in the container before the slag scraping operation starts, which is calculated as described above. Then, the sulfur component content in the molten metal when being processed in a post-process can be estimated by using this calculated sulfur component content in the slag in the container after the slag scraping operation has started and the sulfur component content in the molten metal after desulfurization refining calculated by using the sample analysis as described above, in consideration of the returning rate of sulfur from the slag to the molten metal when being processed in the post-process.

Therefore, the residual ratio of slag can be decided in accordance with the content rate of a sulfur component required in a molten metal (ending of the slag scraping operation can be decided). Accordingly, the present embodiment has an advantage in which adjustment of the component in the molten metal in the post-process can be optimized.

EXAMPLES

Next, Examples performed to check the operational effects of the present invention will be described.

The slag volume evaluation method according to the present embodiment and a method disclosed in Patent Document 1 were compared with each other.

Specifically, a skilled operator performed a slag scraping operation such that the slag scraping rate of the slag S when the slag scraping operation ended was within 0.7 to 0.8, while checking the molten metal surface in the container 4 in a visually recognizing manner. At the time of this slag scraping operation, the residual ratio Ps(t) of the slag S when the slag scraping operation ended was calculated by using the slag volume evaluation method according to the present embodiment, and the slag scraping rate of the slag S was obtained by the foregoing Expression (5). In addition, at the time of this slag scraping operation, the residual ratio of the slag S was calculated according to the areas of the slag S before the slag scraping operation started and when the slag scraping operation ended, which were calculated by using the method disclosed in Patent Document 1, and the slag scraping rate of the slag S was obtained by the foregoing Expression (5).

Figure 7:
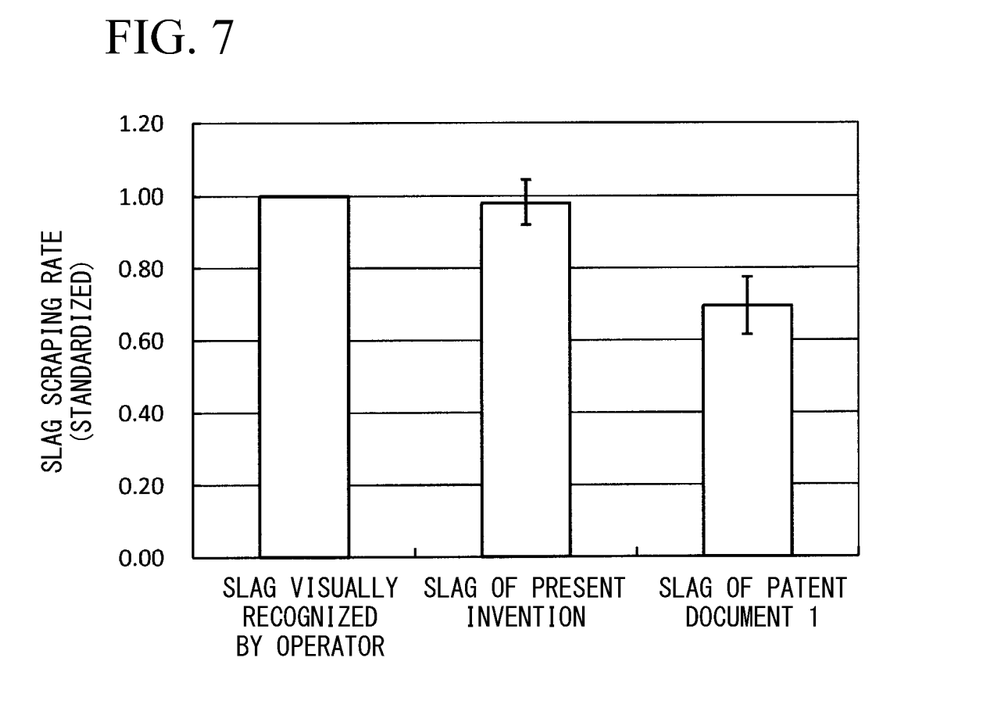
FIG. 7 is a view showing test results in which the slag volume evaluation method and a method disclosed in Patent Document 1 are compared to each other.

The foregoing test was repeated three times. FIG. 7 shows the results.

FIG. 7 shows standardized values of the slag scraping rate of the slag S obtained by using the slag volume evaluation method according to the present embodiment and the slag scraping rate of the slag S obtained by using the method disclosed in Patent Document 1 while having the slag scraping rate of the slag S determined by an operator in a visually recognizing manner as the standard. In FIG. 7, a value in a bar graph indicates the average value of the tests performed three times, and the bars vertically extending in the bar graph indicate the fluctuations (standard deviation 1σ).

As shown in FIG. 7, the slag scraping rate of the slag S obtained by using the method disclosed in Patent Document 1 was 0.70±0.08. In contrast, the slag scraping rate of the slag S obtained by using the slag volume evaluation method according to the present embodiment was 0.98±0.06. That is, it was assumed that the slag scraping rate of the slag S by the slag volume evaluation method according to the present embodiment was closer to that obtained by the sense of the skilled operator and was more accurate than the slag scraping rate by the method disclosed in Patent Document 1.

Hereinabove, the embodiment of the present invention has been described. However, the foregoing embodiment is presented as an example, and the scope of the present invention is not limited to only the foregoing embodiment. The foregoing embodiment can be performed in various other forms, and various types of omissions, replacements, and changes can be made within a range not departing from the gist of the invention. The foregoing embodiment and its modification are included within the invention disclosed in the claims and the range equivalent thereto, similar to being included within the scope and the gist of the invention.

For example, the foregoing embodiment shows a case where the approximation curve (refer to FIG. 5) expressed by the foregoing Expression (1) is calculated in the preparing step ST1. Since the relationship between the thickness K and the density I of slag as shown in FIG. 5 is obtained in the preparing step ST1 according to radiation light of the molten metal M which is incident on the first image capturing unit 1 and is transmitted through the slag S, there are many cases where the thickness K and the density I can be approximated with the exponential function as in Expression (1). However, the approximation curve is not limited to Expression (1) and need only to be capable of fitting the measurement data of the thickness and the density of slag.

For example, an approximation curve expressed by the following Expression (6) or Expression (7) may be calculated.

$$I = I_0/(aK^2 + bK + 1) \quad (6)$$

$$I = I_0/(aK^3 + bK^2 + cK + 1) \quad (7)$$

In addition, for example, the foregoing embodiment shows a case where the thickness K of the slag S is measured in the preparing step ST1 (refer to FIG. 1) according to an image captured by the second image capturing unit 3, in a state where the lower surface of the scraping plate 51 substantially coincides with the lower surface of the slag S (upper surface of the molten metal M). However, in place of the second image capturing unit 3, for example, a pair of laser distance meters which are non-contact distance meters disposed at the same height as each other above the scraping plate 51 may be used. In this case, the distance to the upper surface of the slag S is measured by one laser distance meter, and the distance to the upper surface of the arm 52 is measured by the other laser distance meter. Thereafter, the measurement result of the other laser distance meter is subtracted from the measurement result of one laser distance meter, and the dimension of the arm 52 in the vertical direction is subtracted, so that the distance H1 between the lower surface of the arm 52 and the upper surface of the slag S can be calculated. The thickness K of the slag S may be measured by subtracting the distance H1 calculated in this manner from H0.

In addition, for example, by using the pair of laser distance meters, the thickness K of the slag S may be measured according to the difference between these measurement results by measuring the distance to the upper surface of the slag S using one laser distance meter and measuring the distance to the surface of the molten metal M using the other laser distance meter. In addition, the thickness K of the slag S may be measured by using a measuring rod. In these cases, there is no need to measure the distance H1.

In addition, for example, the foregoing embodiment is separately provided with the first image capturing unit 1 which is used for the purpose of obtaining a captured image for evaluating the volume of the slag S in the slag volume calculating step ST3, and the second image capturing unit 3 which is used for the purpose of calculating the thickness K of the slag Sin the preparing step ST1. However, for example, the second image capturing unit 3 may be used for the purpose of calculating the thickness K of the slag S and may be simultaneously used for purpose of obtaining a captured image for evaluating the volume of the slag S. Here, there is a need for the second image capturing unit 3 to perform image capturing from above oblique to the vertical direction in order to calculate the distance H1 between the lower surface of the arm 52 and the upper surface of the slag S. Therefore, there is concern that when the visual-line angle θ increases, the difference in resolution per pixel between a part on a side closer to the second image capturing unit 3 and a part on a side farther therefrom on the molten metal surface of the container 4 will increase, and even if the thickness of the slag S is the same as each other, a difference will be caused between the densities in the pixel regions. In this manner, since there is concern that the calculation accuracy in the volume of slag will be adversely affected, it is preferable to use the first image capturing unit 1 and the second image capturing unit 3 as in the foregoing embodiment.

In addition, for example, in the foregoing embodiment, the first image capturing unit 1 is adjusted such that the density in the pixel region corresponding to the molten metal M in a captured image obtained by the first image capturing unit 1 becomes 255 (white), that is, the absolute maximum value. In the foregoing embodiment, the density of pixels constituting a captured image is converted into the thickness of the slag S. Therefore, in order to enhance the resolution of calculating the thickness of the slag S, the range of the density in the pixel region corresponding to the slag S can be widely ensured by limiting the range of the density in the pixel region corresponding to the molten metal M other than the slag S to the absolute maximum value. However, for example, the first image capturing unit 1 may be adjusted such that the density in the pixel region corresponding to the molten metal M is within 250 to 255 (such that the densities other than the absolute maximum value are also included). In this case, as the density $I_0$ in the foregoing Expression (1), Expression (2), and Expression (3), the minimum value (250 in the foregoing example) of the density in the pixel region corresponding to the molten metal M may be used.

In addition, in the foregoing embodiment, as shown in FIG. 5, the approximation curve expressed by the foregoing Expression (1) is calculated. Here, regarding the coefficient a in Expression (1), the thickness and the density of slag are measured while changing the component of the slag and the temperature of a molten steel. Consequently, it has been ascertained that the coefficient a is approximately uniform without depending on the component of slag and the temperature of a molten steel. Therefore, when an approximation curve indicating the correspondence between the thickness K and the density I of slag are obtained once, even if the component of slag and the temperature of a molten steel change, the approximation curve can be used. Here, from the viewpoint of calculating the volume of slag more accurately, it is preferable to calculate the approximation curve indicating the correspondence between the thickness K and the density I of slag every time the component of slag and the temperature of a molten steel change.

BRIEF DESCRIPTION OF THE REFERENCE SYMBOLS

1 first image capturing unit
2 image processor
3 second image capturing unit
4 container
5 slag scraping apparatus
100 slag volume evaluation apparatus
M molten metal
S slag

What is claimed is:

1. A slag volume evaluation method for a molten metal surface, in which a volume of slag floating on a surface of a molten metal contained in a container is evaluated according to a captured image of a molten metal surface in the container, the method comprising:

calculating an approximation curve indicating a correspondence between a thickness of the slag and a density parameter in advance by measuring thicknesses of a plurality of pieces of the slag which float on the surface of the molten metal and differ from each other in thickness, and calculating a value of the density parameter which is correlated to a density in a pixel region corresponding to the plurality of pieces of the slag in the captured image obtained by capturing an image of the molten metal surface in the container in a state where the plurality of pieces of the slag are floating on the surface of the molten metal;

capturing the image of the molten metal surface which is an evaluation target; and calculating the volume of the slag by calculating the thickness of the slag for each of pixels constituting the captured image obtained through the capturing, and integrating the calculated thickness of the slag for each of the pixels, according to the value of the density parameter of each of the pixels constituting the captured image obtained through the capturing and the approximation curve calculated through the calculating of the approximation curve.

2. The slag volume evaluation method for a molten metal surface according to claim 1, further comprising:

scraping off the slag from the container; and calculating a residual ratio of the slag in the container, wherein in the capturing, images of the molten metal surface in the container before the scraping and the molten metal surface in the container after the scraping are captured, wherein in the calculating of the volume of the slag, the volume of the slag in the container before the scraping and the volume of the slag in the container after the scraping are calculated, and wherein in the calculating of the residual ratio of the slag, the residual ratio of the slag in the container is calculated by dividing the volume of the slag in the container after the scraping by the volume of the slag in the container before the scraping.

* * * * *

UNITED STATES PATENT AND TRADEMARK OFFICE
CERTIFICATE OF CORRECTION

PATENT NO. : 10,845,352 B2
APPLICATION NO. : 16/466154
DATED : November 24, 2020
INVENTOR(S) : Tomoyuki Kusunoki et al.

It is certified that error appears in the above-identified patent and that said Letters Patent is hereby corrected as shown below:

On the Title Page

Item (73), please correct the Assignee's name from:
"NIPPON STEEL CORPOATION, Tokyo (JP)"
To:
--NIPPON STEEL CORPORATION, Tokyo (JP)--.

Signed and Sealed this
Twenty-sixth Day of January, 2021

Drew Hirshfeld
*Performing the Functions and Duties of the*
*Under Secretary of Commerce for Intellectual Property and*
*Director of the United States Patent and Trademark Office*